United States Patent [19]
von der Heyde

[11] Patent Number: 5,998,762
[45] Date of Patent: Dec. 7, 1999

[54] TICK REMOVAL DEVICE AND METHOD

[76] Inventor: Christian P. von der Heyde, 182 Great Hill Rd. Ext., East Sandwich, Mass. 02537

[21] Appl. No.: 09/039,451

[22] Filed: Mar. 16, 1998

[51] Int. Cl.⁶ .................................................. H05B 1/00
[52] U.S. Cl. .............................................. 219/229; 219/227
[58] Field of Search .................. 219/229, 227, 219/230; 606/131; 294/99.2; 128/303 R

[56] References Cited

U.S. PATENT DOCUMENTS

| | | | |
|---|---|---|---|
| 3,980,861 | 9/1976 | Fukunaga | 219/230 |
| 5,116,347 | 5/1992 | Butler | 606/131 |
| 5,246,449 | 9/1993 | Webster | 606/131 |
| 5,554,161 | 9/1996 | Thibeault | 606/131 |
| 5,556,563 | 9/1996 | Von Der Heyde et al. | 219/227 |

*Primary Examiner*—John A. Jeffery
*Assistant Examiner*—Quang Van
*Attorney, Agent, or Firm*—William Nitkin

[57] ABSTRACT

A device and method for removal of a tick from the skin of a host, such device having an open-ended casing for receiving the tick in a V-shaped slot defined in the casing, such tick to be trapped at the narrow end of the slot with means to apply heat in proximity to the tick to cause it to release its grip from the skin of the host after which it can be removed.

2 Claims, 2 Drawing Sheets

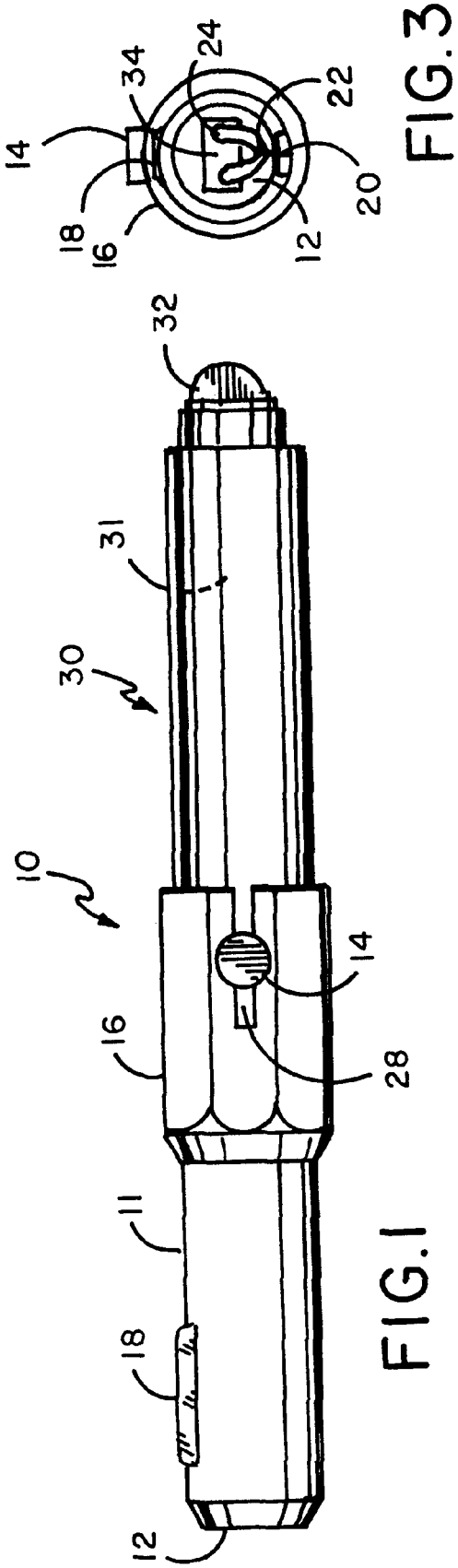
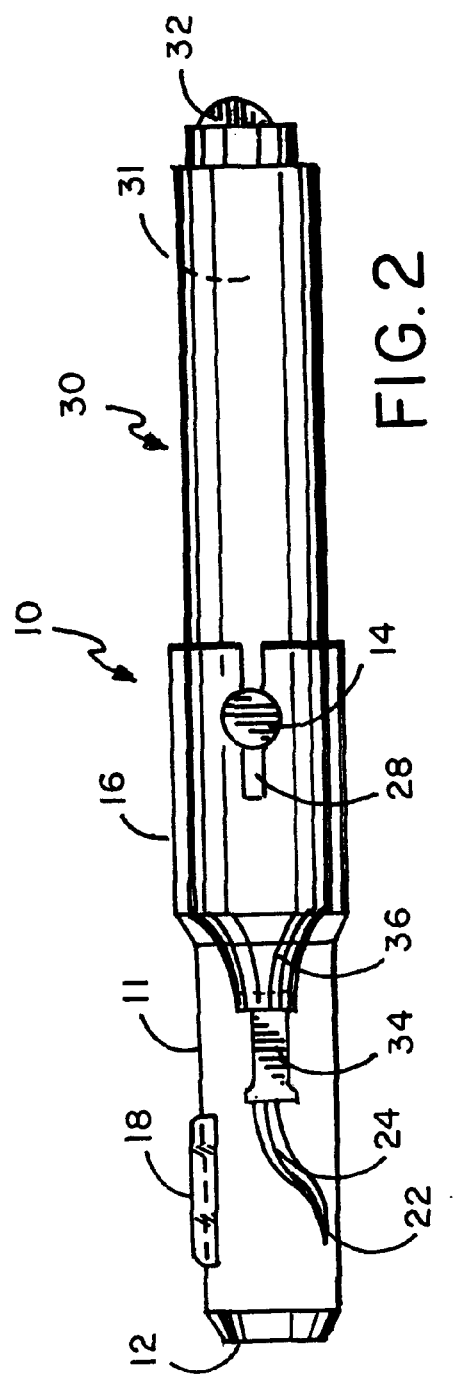

TICK REMOVAL DEVICE AND METHOD

BACKGROUND OF THE INVENTION

1. Field of the Invention

This invention resides in the area of devices for removing ticks from people and animals and more particularly relates to a device having a casing with a tapered slot for engaging a tick within the slot and a heating element in close proximity to the tick for heating the tick to cause it to release its grip whereupon the tick can be removed.

2. Description of the Prior Art

Hand-held devices with tweezer-like arms for removing ticks are well known in the prior art. U.S. Pat. No. 5,556,563 by the present inventor discloses a device having first and second tweezer arms disposed within a casing with the tweezer arms extendible through the casing to grasp a tick. Other examples include U.S. Pat. No. 4,213,460 to Weiner describing a forceps with an electrical current passing therethrough to provide heat, with the forceps having oppositely-aligned, cup-shaped members to surround and remove a tick. U.S. Pat. No. 4,979,771 to Childs, III also describes the use of cup members at the end of tweezer-like elements to surround a tick. U.S. Pat. No. 5,276,306 to Huffman teaches the use of a heated needle which, when poked into a tick, causes the tick to release its grip, and the tick can then be scooped off the skin by a spoon member disposed below the needle. A disadvantage of these tweezer-like gripping devices is their difficulty of use, as manipulating a device to grip a tiny tick requires dexterity sometimes not possessed by the user.

SUMMARY OF THE INVENTION

It is an object of this invention to provide a portable, effective device and method to remove a tick attached to the skin of a person or animal, such device having a casing with a unique tapered V-shaped slot for engaging and grasping a tick and a heating element in close proximity to the held tick for causing the tick to release its grip. In operation, the device is slid across the skin to grasp a tick, the tick becoming trapped in the narrow end of the V-shaped slot defined in the front portion of the casing. The user then activates the heating element which is either in contact with, or in close proximity to, the trapped tick. The heat causes the tick to release its grip on the person or animal, and the tick can then be conveniently lifted away in the casing for easy disposal.

It is a further object of this invention to provide a heat-producing tick removal device where the heating element during use of the device is safely kept away from the skin of the person or animal, the skin being shielded by the bottom part of the plastic casing.

It is a further object of this invention to provide a portable, inexpensive, easily manipulatable device which can operate on a single AA battery.

BRIEF DESCRIPTION OF THE DRAWINGS

FIG. 1 illustrates a side view of the tick removal device of this invention.

FIG. 2 illustrates a side view of the device with the casing shown as being transparent.

FIG. 3 illustrates a front cross-sectional view through the device of this invention.

DESCRIPTION OF THE PREFERRED EMBODIMENT(S)

Figure 4:
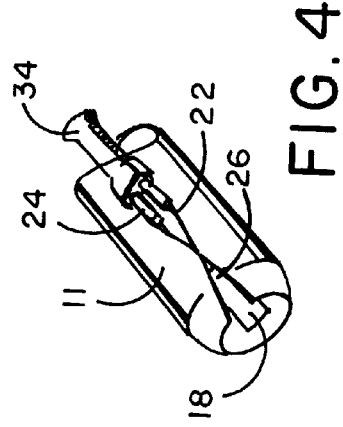
FIG. 4 illustrates a bottom perspective sectional view of the device of this invention.

FIG. 1 illustrates a side view of the tick removal device 10 of this invention showing casing 16 which is slidably mounted on the body 30 of tick removal device 10. Casing 16 is hollow on the inside and can be made of any lightweight durable plastic or equivalent material. Casing 16 has an opening 12 at its front end where the tick is entered into the casing by manually moving the casing to align its open end with the tick and moving the casing forward toward the tick so that the tick passes into the V-shaped slot as described below. From opening 12, casing 16 has a constant diameter of approximately ½ inch for a length of approximately two inches, the diameter thereafter increasing to accommodate a close fit between casing 16 and body 30 of the tick removal device. As seen in FIGS. 1 and 2, casing 16 has an aperture 28 defined within its top portion which allows for movement of activating button 14 therein. A magnifying glass 18 can be mounted on the top of casing 16 near the front end to magnify the size of a tick, facilitating capture of the tick by the user of the device.

As seen in FIG. 2, body 30 of the tick removal device includes heating element 22 which protrudes into the hollow casing. The heating element includes heating element support 34 which can be made of plastic with wires running therethrough. Leads 24 emerge from heating element support 34, which leads are connected to heating element 22. Heating element 22 is part of a circuit which is completed by button 14 which activates as a switch to direct current from a power source, such as a AA battery, in body 30 to heating element 22 which is used to direct heat to a trapped tick. Heating element 22 can be a nichrome wire. Alternatively, the heating element could comprise a small quartz halogen light used to direct a hot beam of light on a tick. The circuit is formed between heating element 22, leads 24, and wires (not shown) which run through support 34 and tapered section 36 of body 30 and are connected to a battery power source with a switch to open and close the circuit. As seen in FIG. 3, a foil strip 20 or equivalent insulative material covers the bottom of casing 16, thereby preventing charring or melting of the casing from the heat produced by the heating element.

Body 30 in a preferred embodiment can be generally tubular in shape and of a size to accommodate the heating element and battery chamber 31 which receives a AA battery to power the circuit. Battery cover 32 fits over the rear end of the device. This battery serves as the power source for the circuit. Heating occurs when the user pushes on activating button 14 which closes a switch, completing the circuit between the battery and the heating element. As seen in FIG. 3, activating button 14 protrudes above the casing of the tick removal device. Although a button activation means is illustrated, other well-known activation means can be utilized in the device of this invention.

Figure 6:
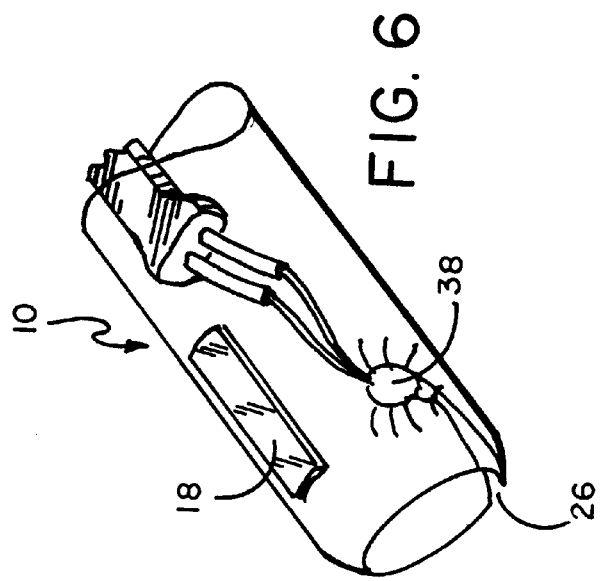
FIG. 6 illustrates the view of FIG. 5 showing the tick caught inside the narrow end of the V-shaped slot disposed in the casing of the device.
Figure 5:
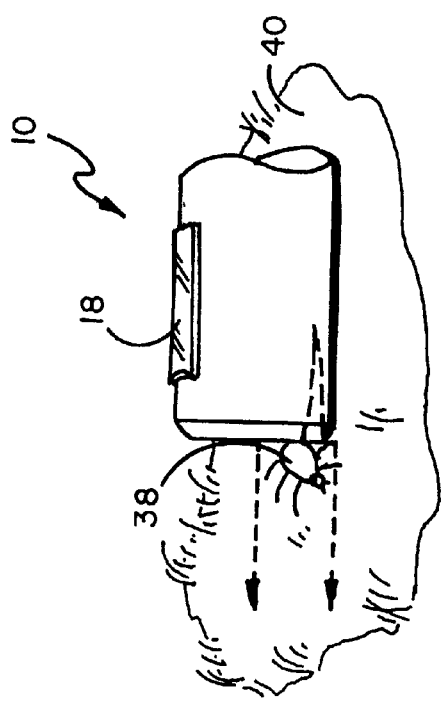
FIG. 5 illustrates a perspective sectional view of the front end of the casing as it is being slid toward a tick to engage the tick in the narrow end of the V-shaped slot.

FIG. 4 shows the unique V-shaped slot in plastic casing 16 which is used to trap the tick. Disposed at the bottom portion and open front end 12 of casing 16 is V-shaped slot 26 which progressively narrows from open front end 12. The slot is essentially cut out of plastic casing 16 and is designed to catch and hold the tick either in contact with, or in close proximity to, heating element 22. The thickness of the casing can be thin enough to pass between the junction of the tick's head and its body which area forms a convenient place to catch and retain the tick until it is removed by the user of the device of this invention. In operation of the device, as seen in FIG. 5, casing 16 is slid along the skin 40 of the host toward tick 38 with the user manually directing the device such that the tick passes into the V-shaped slot. The user can look through magnifying glass 18 located directly over the V-shaped slot to more easily control the direction of the device as it is moved toward the tick. The triangular shape of slot 26 further facilitates directing the device toward the tick. As the casing is moved with the slot advancing around the tick, eventually the distance between the sides of the V-shaped slot adjacent to the tick becomes narrower than the tick's body which sides snugly catch the tick in the narrow portion of the slot since the tick usually does not release its grip on the skin of its host. Once the tick is caught, the heat from the heating source causes the tick to release its grip and its body remains caught in the slot until it is removed by the user. In a preferred embodiment the width of the slot at the front end opening of the casing is approximately ⅛–¼ inch and the sides of the slot are angularly tapered for a distance of approximately ½–¾ inch at which point the sides come together to form a V-shape. As seen in FIG. 6, the head area of tick 38 is shown trapped in the narrowest portion of V-shaped slot 26. In use, the heating element is then activated and produces a surge of heat when the user presses button 14 to activate heating element 22 which is positioned at the narrow end of slot 26 to be close to, or in contact with, the tick's body once it is trapped at the end of slot 26. The intense heat causes the tick to release its grip on the skin of the host whereupon the tick, still trapped in the slot, can be removed.

Although the present invention has been described with reference to particular embodiments, it will be apparent to those skilled in the art that variations and modifications can be substituted therefor without departing from the principles and spirit of the invention.

I claim:

1. A device for removing a tick from the skin of a host, said device for use by a user, comprising:

a casing having a front end and a rear end, said casing having an opening defined at said front end;

a V-shaped slot defined in said casing at said front end of said casing, said slot having a first end disposed at said front end of said casing and a second end, said first end of said slot having a width, said slot being widest at said front end of said casing and coming to a point at said second end;

heating means disposed in proximity to said second end of said V-shaped slot, said heating means having activation means associated therewith; and window means disposed in said casing above said V-shaped slot to aid said user in observing the engagement of said tick within said V-shaped slot.

2. The device of claim 1 further including magnification means disposed in said window means.

* * * * *